(12) United States Patent
Takigawa et al.

(10) Patent No.: US 6,291,735 B1
(45) Date of Patent: Sep. 18, 2001

(54) PROCESS FOR PREPARATION OF HIGH-PURITY INDENE

(75) Inventors: Yasuyuki Takigawa; Hiromi Nakaoka, both of Tokyo (JP)

(73) Assignee: ADCHEMCO Corporation, Tokyo (JP)

( * ) Notice: Subject to any disclaimer, the term of this patent is extended or adjusted under 35 U.S.C. 154(b) by 0 days.

(21) Appl. No.: 09/398,039

(22) Filed: Sep. 17, 1999

(30) Foreign Application Priority Data

Jul. 7, 1999 (JP) .................................................. 11-193400

(51) Int. Cl.[7] ...................................................... C07C 7/14
(52) U.S. Cl. ............................................. 585/812; 585/817
(58) Field of Search ..................................... 585/812, 817

(56) References Cited

U.S. PATENT DOCUMENTS 1,943,078 * 1/1934 Kahl ...................................... 585/812

* cited by examiner

*Primary Examiner*—Walter D. Griffin
*Assistant Examiner*—Tam M. Nguyen
(74) *Attorney, Agent, or Firm*—Oblon, Spivak, McClelland, Maier & Neustadt, P.C.

(57) ABSTRACT

A process is provided for the preparation of high-purity indene. According to the process, impurities are eliminated by crystallization from an indene stock which is available in a concentrated form by distillation of a coal tar fraction and/or a petroleum fraction. High-purity indene having a purity of 99 wt. % or higher can be obtained.

9 Claims, 1 Drawing Sheet

PROCESS FOR PREPARATION OF HIGH-PURITY INDENE

BACKGROUND OF THE INVENTION a) Field of the Invention

This invention relates to a process for preparing high-purity indene from a coal tar fraction and/or a petroleum fraction, and also to high-purity indene.

b) Description of the Related Art

Indene which is contained in coal tar and petroleum residues is used as coumarone-indene resin, modifiers upon production of synthetic resins, and raw materials for various medicines, agrichemicals and other synthetic products. Upon separating and recovering such indene from coal tar and/or petroleum distillation residues by precision distillation, components having boiling points close to indene, for example, phenol, alkylpyridines, benzonitrile, undecane, alkylbenzenes and the like cannot be fully eliminated, thereby making it difficult to recover indene in a highly-purified form. Among these hardly-eliminative components, tar acids such as phenol and cresol and basic components such as alkylpyridines and aniline can be eliminated by washing with an aqueous acid solution and an aqueous alkali solution.

For example, Japanese Patent Publication No. SHO 62-32731 discloses a process for recovering indene from a tar light oil containing indene at a concentration of about 20 wt. %. According to this process, the tar light oil is distilled to obtain a fraction having an indene concentration of 50 wt. % or higher. After successively washing this fraction with an aqueous acid solution and an aqueous alkali solution, the fraction is distilled again.

This process however cannot eliminate neutral components such as benzonitrile, alkylbenzenes and indane. Concerning elimination of benzonitrile among these neutral components, Japanese Patent Application Laid-Open No. HEI 9-301898 discloses a process for the recovery of indene. According to this process, a solid alkali is added to an indene-containing tar light oil, and the resulting mixture is subjected to heat treatment at a temperature of 100° C. or higher. Subsequent to removal of precipitated insoluble matter, distillation is conducted. This process can eliminate benzonitrile and tar acids, but can hardly remove alkylbenzenes, indane and the like. Moreover, this process also requires treatment of waste water and insoluble matter, both of which are produced in the alkali treatment, leading to an increase in the production cost of the indene so obtained. Even a combined application of the above-described conventional techniques is still unable to fully eliminate alkylbenzenes from indene, so that indene available on an industrial scale from such a combined application is limited only to one having a purity as low as 95 to 97 wt. % or so even at the highest.

As has been described above, the conventional processes for eliminating impurities from indene-containing oils can hardly eliminate alkylbenzenes, and for the elimination of all impurities, plural steps are required. None of the conventional processes are therefore satisfactory for the economical preparation of high-purity indene.

SUMMARY OF THE INVENTION

An object of the present invention is therefore to solve the problems of these conventional processes and to provide a process for the preparation of high-purity indene, which permits substantially full elimination of impurities led by alkylbenzenes and including benzonitrile by simple operations. Another object of the present invention is to provide high-purity indene available from purification.

The present inventors have proceeded with extensive research to achieve the above-described objects of the present invention. As a result, it has been found that use of crystallization for an indene-concentrated fraction (stock) available from distillation of a coal tar and/or a petroleum fraction such that indene alone is crystallized and solidified by chilling or pressurization and solid indene and liquid impurities are subjected to solid-liquid separation makes it possible to eliminate impurities, such as alkylbenzenes, benzonitrile, indane, undecane and basic components, by simple operations.

In one aspect of the present invention, there is thus provided a process for the preparation of high-purity indene, which comprises eliminating, by crystallization, impurities from an indene stock which is available in a concentrated form by distillation of a coal tar fraction and/or a petroleum fraction. In another aspect of the present invention, there is also provided high-purity indene having a purity of at least 99 wt. %.

According to the present invention, benzonitrile, alkylbenzenes, and aliphatic hydrocarbons such as undecane—all of which can hardly be separated from indene by distillation, chemical washing and/or the like—can be effectively eliminated by simple operations from an indene-containing coal tar and/or petroleum fraction, thereby making it possible to prepare indene having a very high purity of 99 wt. % or higher or even of 99.5 wt. % or higher.

DETAILED DESCRIPTION OF THE INVENTION AND PREFERRED EMBODIMENTS

Figure 1:
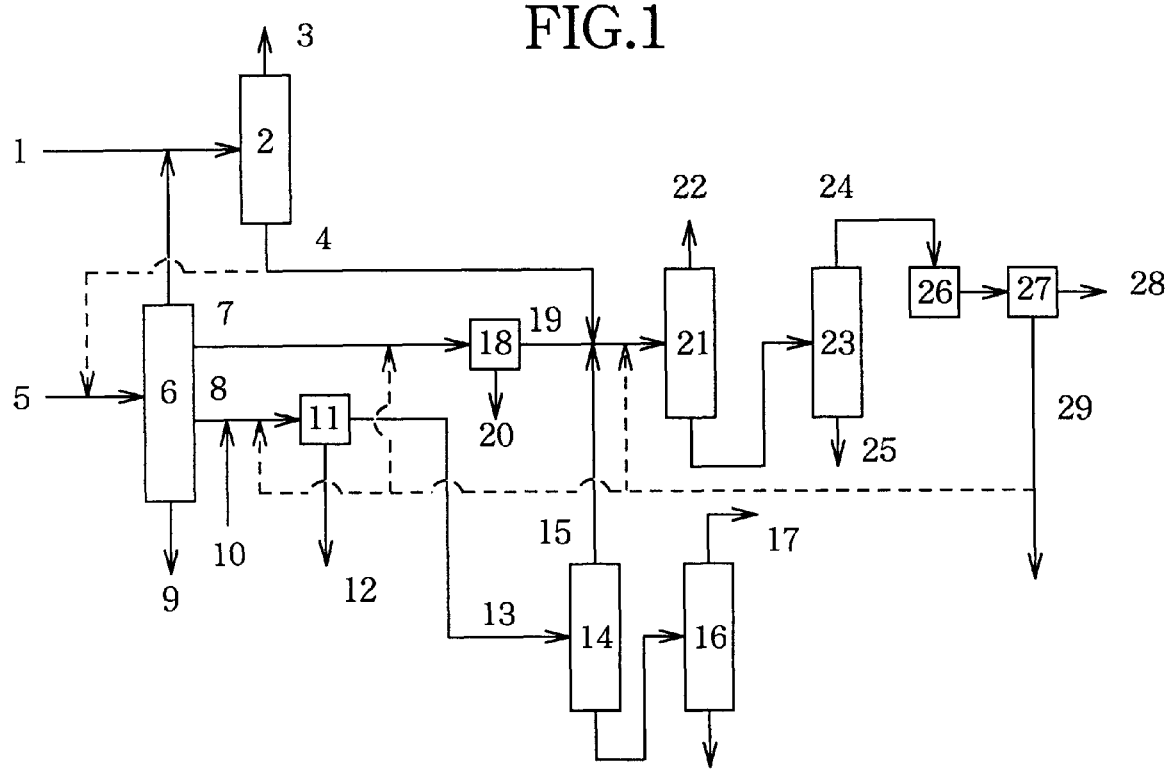
FIG. 1 is a flow diagram showing illustrative steps of the process of the present invention for the preparation of high-purity indene.

The present invention will next be described in further detail on the basis of preferred embodiments.

A stock 24 for use in the present invention is obtained as will be described next. Namely, coal tar 5 is distilled in a coal tar distillation column 6, and a tar acid fraction 7, the bubble point of which ranges from 170 to 210° C., and a naphthalene fraction 8 are drawn as side-stream oils. Designated at numeral 9 is a heavy oil. Caustic soda 10 is added to the naphthalene fraction 8, and in a tar acid extraction tank 11, tar acid 12 contained in the naphthalene fraction 8 is extracted for its separation and recovery. Upon distillation and recovery of naphthalene 17 from the extraction residue 13 through a naphthalene initial-boiling column 14 and a naphthalene distillation column 16, a naphthalene light oil 15 is obtained. Subsequent to extraction of tar acid 20 for its separation and recovery from the tar acid fraction 7 in a tar acid extraction tank 18, a residue 19 is obtained. Further, a residue 4 is obtained after benzene, toluene, xylene and the like 3 are recovered from a petroleum charge 1 in a BTX pre-distillation column 2. From either all or any one or two of the three residues, namely, the residues 4,15,19, components 22 having lower boiling points than indene, such as indane, and components 25 having higher boiling points and also higher solidifying points than indene, such as naphthalene and cresol, are removed by vacuum distillation in a light-ends tower 21 and in a heavy-ends tower 23, whereby a fraction 24 (stock) with indene concentrated to a level in a range of from 70 to 97 wt. % is obtained. The residue from the petroleum charge 1 may be used by mixing it in the coal tar 5.

The stock 24 is chilled to a temperature lower than −10° C., for example, to −20° C. or so in a crystallizer 26, and subsequent to solidification of the stock in its entirety, the solidified stock is ground. When this ground stock is placed in a centrifugal separator 27 controlled in a temperature range of from −10 to 0° C. and is subjected to solid-liquid separation there, impurities other than indene are caused to melt into liquid and indene alone remains as a solid. Accordingly, the impurities and indene separate from each other into a solid 28 and a liquid 29. The solid fraction is high-purity indene 28, which is substantially free of benzonitrile, alkylbenzenes and other impurities. As an alternative, the stock 24 may be chilled to a temperature in a range of from −10 to 0° C. in the crystallizer 26 to make indene precipitate, and the thus-chilled stock may then be subjected at the same temperature to solid-liquid separation in the centrifugal separator 27 such that the chilled stock is separated into a solid 28 and a liquid 29. Incidentally, indene may be added as seed crystals upon chilling. Upon conducting the solid-liquid separation, impurities are more readily liquefied as the temperature of the centrifugal separator becomes closer to the melting point (solidifying point) of indene. High-purity indene, for example, of 99.5 wt. % or higher purity can be obtained accordingly. A more preferred temperature range is from −6 to −2° C. As the filtrate obtained by the above-described solid-liquid separation contains indene at a substantial concentration, it is desired to recycle the filtrate to the distillation column 21 or to one or both of the tar acid extraction tanks 11,18. Instead of the above-described chilling in the crystallizer, pressure crystallization which solidifies the stock by applying a pressure may be used.

Further, tar acids having melting points higher than indene and still remaining at low concentrations in the stock immediately before the crystallization or the purified indene, such as phenol and cresol, can be eliminated almost completely by washing the stock with an alkali shortly before the crystallization or treating the purified indene with an alkali after the crystallization.

Physical properties of components, which have boiling points in a range of from 170 to 195° C. and have high probability of being contained in indene fractions, are shown below in Table 1. Except for acidic oils, there is no component having a solidifying point (melting point) higher than indene. The present invention therefore makes it possible to fully separate these components by the above-described crystallization, although distillation can hardly separate them. According to the present invention as described above, high-purity indene having a purity of 99 wt. % or higher or even of 99.5 wt. % or higher can be provided although such high-purity indene has been unavailable to date.

TABLE 1

| Classification | Name of component | Boiling point (° C.) | Solidifying point (° C.) | Confirmation by reagent addition |
|---|---|---|---|---|
| Neutral oils | Indene | 182 | −2 | Confirmed |
| | Indane | 178 | −15 | Confirmed |
| | Undecane | 196 | −26 | Confirmed |
| | 1-Undecene | 193 | −49 | Confirmed |
| | Benzonitrile | 191 | −13 | Confirmed |
| C4-Alkyl-benzenes (neutral oils) | n-Butylbenzene | 183 | −88 | Confirmed |
| | sec-Butylbenzene | 173 | −76 | Confirmed |
| | tert-Butylbenzene | 170 | −58 | Confirmed |
| | iso-Butylbenzene | 171 | −52 | Not confirmed |
| | 2-Isopropyltoluene | 178 | −72 | Not confirmed |
| | 3-Isopropyltoluene | 175 | −64 | Not confirmed |
| | 4-Isopropyltoluene | 177 | −68 | Confirmed |
| | 2-Propyltoluene | 185 | −60 | Confirmed |
| | 3-Propyltoluene | 182 | −83 | Confirmed |
| | 4-Propyltoluene | 183 | −64 | Confirmed |
| C4-Alkyl-benzenes (neutral oils) | 1,4-Diethylbenzene | 182 | −43 | Confirmed |
| | 1,3-Diethylbenzene | 181 | −84 | Confirmed |
| | 1,2-Diethylbenzene | 184 | −31 | Confirmed |
| | 5-Ethyl-1,3-dimethylbenzene | 184 | −84 | Confirmed |
| | 4-Ethyl-1,3-dimethylbenzene | 188 | −63 | Confirmed |
| | 2-Ethyl-1,3-dimethylbenzene | 190 | −16 | Confirmed |
| | 4-Ethyl-1,2-dimethylbenzene | 190 | −67 | Confirmed |
| | 3-Ethyl-1,2-dimethylbenzene | 194 | −50 | Confirmed |
| | 2-Ethyl-1,4-dimethylbenzene | 187 | −54 | Confirmed |
| Basic oils | 2,4,6-Trimethylpyridine | 171 | −44 | Confirmed |
| | 2,3,6-Trimethylpyridine | 177 | −12 | Not confirmed |
| | 5-Ethyl-2-methylpyridine | 178 | −71 | Not confirmed |
| Acidic oils | Phenol | 182 | 41 | Confirmed |
| | o-Cresol | 191 | 30 | Confirmed |

(Definition of C4-alkylbenzenes)

The term "C4-alkylbenzenes" as used in the present invention has been defined as will be described hereinafter.

From standard samples added with the reagents which are indicated as "confirmed" out of the C4-alkylbenzenes shown in Table 1, many of the C4-alkylbenzenes were detected between indene and 1-undecene on GC charts. The sum of peaks detected between the peaks of these compounds has therefore been defined as the total content of C4-alkylbenzenes. The content of 5-ethyl-1,3-dimethylbenzene, which was contained at a highest concentration among C4-alkylbenzenes, and that of o-cresol are however shown independently. It is to be noted that the components added as reagents to prepare the standard samples are not all contained in indene stocks.

The present invention will next be described more specifically on the basis of Examples and Comparative Examples, in which the designations of "part" or "parts" and "%" are on a weight basis unless otherwise specifically indicated.

Further, analyses were conducted by gas chromatography. Identification of components was confirmed by conducting gas chromatography on standard samples added with the corresponding reagents. Most of the components shown in Table 1 were confirmed in this manner. Among the C4-alkylbenzenes, 5-ethyl-1,3-dimethylbenzene (hereinafter abbreviated as "5-E-1,3-DMB") was contained at the highest concentration, so that its analysis data are shown independently. The contents of the remaining C4-alkylbenzenes are shown collectively in terms of a total value.

EXAMPLE 1

300 parts of an indene fraction (stock) (indene 96.79%, indane 0.31%, benzonitrile 0.73%, 5-E-1,3-DMB 1.35%, other C4-alkylbenzenes 0.41%, undecane 0.15%, others 0.26%) were chilled and solidified at −20° C. The resulting solid was ground and then subjected to solid-liquid separation in a centrifugal separator set at −10° C., whereby 171 parts of crystals (indene 99.17%, indane 0.17%, benzonitrile 0.22%, 5-E-1,3-DMB 0.34%, other C4-alkylbenzenes 0.04%, undecane 0.04%, others 0.02%) were obtained. The compositions of the stock, recovered crystals and filtrate are shown in Table 2.

EXAMPLE 2

Purification was conducted in the same manner as in Example 1 except that the centrifugal separator was set at −6° C., whereby 172 parts of crystals (indene 99.61%, indane 0.15%, benzonitrile 0.11%, 5-E-1,3-DMB 0.11%, other C4-alkylbenzenes 0.00%, undecane 0.01%, others 0.01%) were obtained. The compositions of the stock, recovered crystals and filtrate are shown in Table 2.

EXAMPLE 3

Purification was conducted in the same manner as in Example 1 except that the centrifugal separator was set at −2° C., whereby 123 parts of crystals (indene 99.85%, indane 0.10%, benzonitrile 0.05%, 5-E-1,3-DMB 0.00%, other C4-alkylbenzenes 0.00%, undecane 0.00%, others 0.00%) were obtained. The compositions of the stock, recovered crystals and filtrate are shown in Table 2.

TABLE 2

|  | Stock | Example 1 | | Example 2 | | Example 3 | |
| --- | --- | --- | --- | --- | --- | --- | --- |
|  |  | Crystals | Filtrate | Crystals | Filtrate | Crystals | Filtrate |
| Material balance (parts) | 300 | 171 | 129 | 172 | 128 | 123 | 177 |
| Indene (%) | 96.79 | 99.17 | 93.64 | 99.61 | 93.00 | 99.85 | 94.66 |
| Indane (%) | 0.31 | 0.17 | 0.50 | 0.15 | 0.53 | 0.10 | 0.46 |
| Benzonitrile (%) | 0.73 | 0.22 | 1.41 | 0.11 | 1.56 | 0.05 | 1.20 |
| 5-E-1,3-DMB (%) | 1.35 | 0.34 | 2.69 | 0.11 | 3.02 | 0.00 | 2.29 |
| Other C4-benzenes (%) | 0.41 | 0.04 | 0.90 | 0.00 | 0.96 | 0.00 | 0.69 |
| Undecane (%) | 0.15 | 0.04 | 0.30 | 0.01 | 0.34 | 0.00 | 0.25 |
| Others (%) | 0.26 | 0.02 | 0.56 | 0.01 | 0.59 | 0.00 | 0.45 |

EXAMPLE 4

Purification of 100 parts of an indene fraction (indene 87.22%, indane 1.02%, benzonitrile 2.37%, 5-E-1,3-DMB 2.36%, other C4-alkylbenzenes 1.11%, undecane 0.78%, others 5.14%) was conducted by chilling the indene fraction at −10° C. to cause indene to crystallize out and then subjecting the thus-chilled indene fraction, as it was, to solid-liquid separation in a centrifugal separator set at −10° C., whereby 46 parts of crystals (indene 99.06%, indane 0.42%, benzonitrile 0.22%, 5-E-1,3-DMB 0.00%, other C4-alkylbenzenes 0.00%, undecane 0.00%, others 0.30%) were obtained. The compositions of the stock, recovered crystals and filtrate are shown in Table 3.

EXAMPLE 5

To the entirety of the filtrate produced in Example 4, 46 parts of the indene fraction employed in Example 4 were added to prepare a still further indene fraction. Using 100 parts of this indene fraction as a stock, purification was conducted in the same manner as in Example 4. Crystals were obtained in an amount of 38 parts. The compositions of the stock, recovered crystals and filtrate are also shown in Table 3.

TABLE 3

|  | Example 4 | | | Example 5 | | |
| --- | --- | --- | --- | --- | --- | --- |
|  | Stock | Crystals | Filtrate | Stock | Crystals | Filtrate |
| Material balance (parts) | 100 | 46 | 54 | 100 | 38 | 62 |
| Indene (%) | 87.22 | 99.06 | 77.13 | 81.77 | 98.95 | 71.36 |
| Indane (%) | 1.02 | 0.42 | 1.53 | 1.30 | 0.46 | 1.82 |
| Benzonitrile (%) | 2.37 | 0.22 | 4.20 | 3.36 | 0.37 | 5.19 |
| 5-E-1,3-DMB (%) | 2.36 | 0.00 | 4.37 | 3.45 | 0.03 | 5.55 |
| Other C4-benzenes (%) | 1.11 | 0.00 | 2.06 | 1.62 | 0.02 | 2.60 |
| Undecane (%) | 0.78 | 0.00 | 1.44 | 1.14 | 0.01 | 1.83 |
| Others (%) | 5.14 | 0.30 | 9.27 | 7.36 | 0.36 | 11.65 |

COMPARATIVE EXAMPLE 1

To 100 parts of an indene fraction (indene 96.79%, indane 0.38%, benzonitrile 0.32%, 5-E-1,3-DMB 1.67%, other C4-alkylbenzenes 0.28%, undecane 0.07%, others 0.49%), an equal amount of a 10% NaOH aqueous solution was added. Under stirring, the resultant mixture was heated at 90° C. for 7 hours to perform hydrolytic treatment. The reaction mixture was allowed to cool down, and was then left over standstill to subject it to oil-water separation. The oil layer was washed with an equal amount of water, whereby 87 parts of indene (indene 97.11%, indane 0.39%, benzonitrile 0.00%, 5-E-1,3-DMB 1.74%, other C4-alkylbenzenes 0.29%, undecane 0.08%, others 0.39%) were obtained. The compositions of the stock, alkali-treated indene and water-washed indene are shown in Table 4.

TABLE 4

|  | Comparative Example 1 | | |
| --- | --- | --- | --- |
|  | Stock | After alkali treatment | After water washing |
| Material balance (parts) | 100 |  | 87 |
| Indene (%) | 96.79 | 97.18 | 97.11 |
| Indane (%) | 0.38 | 0.38 | 0.39 |
| Benzonitrile (%) | 0.32 | 0.00 | 0.00 |
| 5-E-1,3-DMB (%) | 1.67 | 1.70 | 1.74 |
| Other C4-benzenes (%) | 0.28 | 0.30 | 0.29 |
| Undecane (%) | 0.07 | 0.08 | 0.08 |
| Others (%) | 0.49 | 0.36 | 0.39 |

COMPARATIVE EXAMPLE 2

To 100 parts of an indene fraction (indene 88.95%, indane 1.05%, benzonitrile 0.81%, 5-E-1,3-DMB 3.26%, other C4-alkylbenzenes 1.50%, undecane 1.44%, phenol 0.38%, o-cresol 0.25%, bases 6695 ppm, others 2.36%), 11 parts of a 20% $H_2SO_4$ aqueous solution was added. After stirring, the reaction mixture was left over standstill. The separated oil layer was then washed likewise with 5 parts of a 10% NaOH aqueous solution, and the oil layer was washed further with 102 parts of water. The indene (95 parts) obtained by these chemical washing was then subjected to distillation for the removal of water, whereby 74 parts of purified indene (indene 90.63%, indane 0.75%, benzonitrile 0.57%, 5-E-1, 3-DMB 3.31%, other C4-alkylbenzenes 1.53%, undecane 1.24%, phenol 0.00%, o-cresol 0.00%, bases 10 ppm or less, others 1.97%) were recovered. The compositions of the stock, chemical-treated indene and distilled indene are shown in Table 5.

TABLE 5

|  | Comparative Example 2 | | |
| --- | --- | --- | --- |
|  | Stock | After chemical treatment | After distillation |
| Material balance (parts) | 100 | 95 | 74 |
| Indene (%) | 88.95 | 89.71 | 90.63 |
| Indane (%) | 1.05 | 1.04 | 0.75 |
| Benzonitrile (%) | 0.81 | 0.75 | 0.57 |
| 5-E-1,3-DMB (%) | 3.26 | 3.35 | 3.31 |
| Other C4-benzenes (%) | 1.50 | 1.66 | 1.53 |
| Undecane (%) | 1.44 | 1.39 | 1.24 |
| Phenol (%) | 0.38 | 0.00 | 0.00 |
| o-Cresol (%) | 0.25 | 0.00 | 0.00 |
| Others (%) | 2.36 | 2.10 | 1.97 |
| Bases (including others) (ppm) | 6,695 | $\geq 10$ | $\geq 10$ |

COMPARATIVE EXAMPLE 3

Purification was conducted in the same manner as in Example 1 except that the centrifugal separator was set at 2° C. No crystals were obtained, and indene was recovered solely as a filtrate.

COMPARATIVE EXAMPLE 4

Purification was conducted in the same manner as in Example 1 except that the centrifugal separator was set at −20° C. No thawed out filtrate was obtained.

This application claims the priority of Japanese Patent Application No. HEI 11-193400 filed Jul. 7, 1999, which is incorporated herein by reference.

What is claimed is:

1. A process for preparing high-purity indene comprising:
    chilling an indene stock comprising a distilled coal tar fraction and/or a distilled petroleum fraction, to a temperature of −20 to −10° C. thereby forming crystallized indene therein,
    subjecting said cooled indene stock to solid-liquid separation in a centrifugal separator at a temperature of −10 to 0° C., thereby eliminating impurities from said crystallized indene and providing high-purity indene.

2. The process of claim 1, wherein said impurities comprise indane, benzonitrile, aliphatic hydrocarbons and C4-alkylbenzenes.

3. The process of claim 1, wherein said indene stock is substantially free of substances having solidifying points higher than indene.

4. The process of claim 1, comprising:

chilling said indene stock into a solidified product;

grinding said solidified product into a ground product; and subjecting said ground product to solid-liquid separation by a centrifugal separator at a temperature of from −10 to 0° C.

5. The process of claim 1, wherein a filtrate available from said solid-liquid separation is recycled as a raw material for said indene stock.

6. The process of claim 3, wherein a filtrate available from said solid-liquid separation is recycled as a raw material for said indene stock.

7. The process of claim 1, wherein a filtrate available from said solid-liquid separation is recycled as a raw material for said indene stock.

8. The process of claim 4, wherein a filtrate available from said solid-liquid separation is recycled as a raw material for said indene stock.

9. The process of claim 1, wherein said indene stock is washed with alkali.

* * * * *